US011793876B2

United States Patent
Lupton et al.

(10) Patent No.: US 11,793,876 B2
(45) Date of Patent: Oct. 24, 2023

(54) BULK POLYETHYLENE GLYCOL COMPOSITIONS

(71) Applicant: L. Perrigo Company, Allegan, MI (US)

(72) Inventors: Lisa Kay Lupton, Kalamazoo, MI (US); Kiran Kumar Muppireddy, Portage, MI (US); Inderdeep Bhatia, Kalamazoo, MI (US); Carlos O. Paz, Fairview, NJ (US); Bruce D. Johnson, Byron Center, MI (US)

(73) Assignee: L. PERRIGO COMPANY, Allegan, MI (US)

( * ) Notice: Subject to any disclaimer, the term of this patent is extended or adjusted under 35 U.S.C. 154(b) by 0 days.

(21) Appl. No.: 17/072,707

(22) Filed: Oct. 16, 2020

(65) Prior Publication Data
US 2021/0113698 A1  Apr. 22, 2021

Related U.S. Application Data

(60) Provisional application No. 62/923,009, filed on Oct. 18, 2019.

(51) Int. Cl.
| *A61K 47/26* | (2006.01) |
| *B65D 77/04* | (2006.01) |
| *A61K 9/00* | (2006.01) |
| *A61K 31/77* | (2006.01) |

(52) U.S. Cl.
CPC ............ *A61K 47/26* (2013.01); *A61K 9/0095* (2013.01); *A61K 31/77* (2013.01); *B65D 77/0426* (2013.01)

(58) Field of Classification Search
CPC ...... A61K 47/26; A61K 9/0095; A61K 31/77; A61K 9/1623; B65D 77/0426
See application file for complete search history.

(56) References Cited

U.S. PATENT DOCUMENTS

| 4,093,710 A | 6/1978 | Sass et al. |
| 4,347,235 A | 8/1982 | Daunora |
| 6,432,450 B1 | 8/2002 | Gergely et al. |
| 6,444,198 B1 | 9/2002 | Daggy et al. |
| 6,811,793 B2 | 11/2004 | Wehling |
| 8,956,652 B2 | 2/2015 | Rau |
| 9,457,204 B2 | 10/2016 | Rau et al. |
| 9,560,870 B2 | 2/2017 | Schultz et al. |
| 9,566,300 B2 | 2/2017 | Shaver |
| 9,649,274 B2 | 5/2017 | Stella et al. |
| 10,028,977 B2 | 7/2018 | Stella et al. |
| 10,322,144 B2 | 6/2019 | Stella et al. |
| 10,617,714 B2 | 4/2020 | Stella et al. |
| 2004/0143005 A1* | 7/2004 | Barras ............... A61K 9/009 514/723 |

* cited by examiner

*Primary Examiner* — Matthew P Coughlin
*Assistant Examiner* — Thurman Wheeler
(74) *Attorney, Agent, or Firm* — Honigman LLP; Christopher C. Forbes

(57) ABSTRACT

The present invention relates to bulk dry compositions comprising polyethylene glycol and an additive, such as a flavoring agent and/or sweetener, wherein the additive remains at a consistent concentration throughout the bulk composition. The invention also relates to processes for preparing the bulk dry compositions comprising polyethylene glycol.

27 Claims, 8 Drawing Sheets

BULK POLYETHYLENE GLYCOL COMPOSITIONS

CROSS REFERENCE TO RELATED APPLICATION

This application claims priority to U.S. Provisional Patent Application No. 62/923,009, filed Oct. 18, 2019, the entire contents of which are incorporated herein by reference.

TECHNICAL FIELD OF THE INVENTION

The present invention relates to bulk dry compositions comprising polyethylene glycol and an additive, such as a flavoring agent and/or sweetener, wherein the additive remains at a consistent concentration throughout the bulk composition. The invention also relates to processes for preparing the bulk dry compositions comprising polyethylene glycol.

BACKGROUND OF THE INVENTION

Polyethylene glycol (PEG), particularly PEG 3350 is a known osmotic laxative. Typically, PEG laxative compositions are sold as dry compositions which are to be combined with an aqueous medium to provide a consumable laxative solution. Examples of such products include Miralax® (MSD consumer care) and Gavilax® (Gavis Pharmaceuticals, NJ).

An aqueous PEG solution with no other additives, while functionally viable, does not have a pleasing taste to the consumer, and it is therefore desirable to include a flavoring agent and/or a sweetener. Accordingly, it is desirable to have a dry PEG composition comprising a flavoring agent and/or a sweetener pre-mixed in a single, convenient composition. This composition can then be dissolved in an appropriate amount of water or any other beverages to be consumed as a laxative treatment.

While compositions comprising PEG and other additives, such as flavoring agents and sweeteners, are available in single dose packets, it is difficult to provide a bulk dry composition in a single container. The reason for this is that additives, such as flavoring agents and sweeteners, have a tendency to segregate from PEG at the particulate level. This causes variation in the amount of additive from dose to dose of the bulk composition.

Described herein is a dry bulk PEG composition comprising additives that do not segregate from the PEG, and remain consistent throughout the dry bulk composition.

SUMMARY OF THE INVENTION

The present invention includes a dry bulk PEG composition comprising additives that do not segregate from the PEG, and remain consistent throughout the dry bulk composition. In practice, this improvement allows a dry PEG composition with additives, such as a flavoring agent and/or a sweetener to be packaged in a bulk composition rather than each dose or serving necessitating its own individual packaging.

The present invention allows the introduction of sweetener and/or flavor, while maintaining the physical properties, such as particle size, particle morphology/shape, bulk/tapped density, etc., of the PEG 3350 Active Pharmaceutical Ingredient (API). The present invention also seeks to achieve target weights of the finished product bulk composition in single multiple serving containers, such as plastic bottles, and to ensure appropriate unit dose while measuring with bottle cap. In some embodiments, the unit dose is between 15 g and 20 g. In some further embodiments, the unit dose is 17 g. Internal specifications for PEG 3350 product release include a bulk density of 0.62-0.76 g/mL, and a tapped density of 0.68-0.84 g/mL.

Due to each finished container having multiple servings of the packaged product, a significant improvement of the present invention is the minimization of segregation of flavor and/or sweetener from the PEG particles within the container. Accordingly, the present invention achieves a consistent consumer experience from serving to serving.

The bulk compositions of the present invention also dissolve in a solvent, such as water, to a clear resulting solution, and thus provide a more aesthetically pleasing dosing solution.

The Top Spray Granulation process of the present invention offers the advantage of depositing the flavor and sweetener onto the PEG granules to reduce the potential for segregation of the flavor and/or sweetener from the PEG upon downstream processing, e.g. bottle filling, packaging, shipping, consumer use, etc. The processes of the invention also conserve the physical properties of the PEG API, which are critical for maintaining product fill weights in bottles and consistent allocation of the unit dose through volumetric measurement with the bottle cap. Conserving the physical properties of PEG is also critical to the mechanism of action of this osmotic laxative.

In one aspect, the invention includes a dry component bulk laxative composition comprising polyethylene glycol having a molecular weight between 2500 g/mol and 4000 g/mol, a flavoring agent, and optionally a sweetener, wherein the variation in the amount of sweetener and/or flavoring agent from dose to dose of the bulk composition is minimized throughout the dry component laxative composition.

In another aspect, the invention includes a dry component bulk laxative composition comprising:
  a. about 99.33 wt % polyethylene glycol having an average molecular weight of about 3350 g/mol;
  b. about 0.08 wt % sucralose; and
  c. about 0.58 wt % of a flavoring agent;
  wherein the composition has a bulk density of about 0.610 g/mL, about 0.644 g/mL, about 0.670 g/mL, or about 0.672 g/mL, and a tapped density of about 0.678 g/mL, about 0.700 g/mL, about 0.744 g/ml, or about 0.764 g/mL;
  and wherein the composition consists essentially of PEG powder having no flavor and no sweetener added, and PEG powder combined with flavor and, optionally, sweetener.

In another aspect, the invention includes a process for producing a dry component bulk laxative composition described herein, the process comprising adding the polyethylene glycol, the flavoring agent, and the sweetener, if present, into a blender to form a dry mixture, and blending the dry mixture.

In another aspect, the invention includes a process for producing a dry component bulk laxative composition as described herein, the process comprising:
  a. mixing a first portion of the flavoring agent and a first portion of the sweetener, if present, in a solvent to form a suspension;
  b. spraying and depositing the suspension from step a onto a first quantity of polyethylene glycol using a top spray granulation process to form a first mixture;

c. sifting the first mixture from step b to form a second mixture having a consistent particle size of less than 850 microns (passed through a #20 mesh); and d. optionally, adding to a blender the second mixture from step c, a second quantity of polyethylene glycol, a second portion of the flavoring agent, and a second portion of the sweetener, and blending to produce the dry component bulk laxative composition.

DETAILED DESCRIPTION OF THE INVENTION

Figure 1:
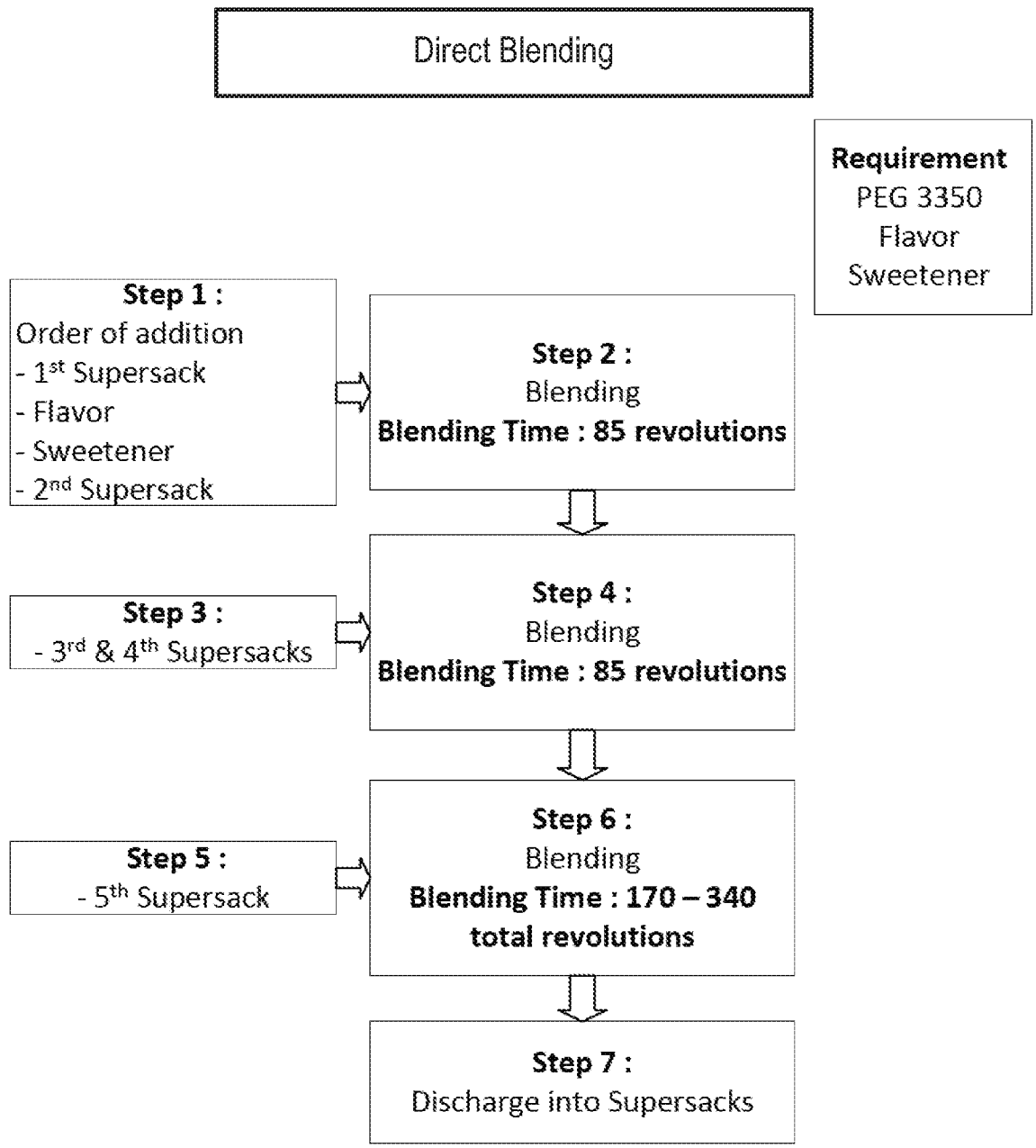
FIG. 1 is a flow chart depicting a direct blending process for producing a single batch of a PEG composition that further comprises a flavoring agent and sweetener.

As used herein, the following definitions shall apply unless otherwise indicated.

Definitions

As used herein, the term "bulk composition" as in "bulk dry composition" or "bulk PEG composition" or "bulk laxative composition" means a single composition of such a weight or volume that two or more individual dosages or servings are provided within a single composition, and that each individual dosage or serving within the bulk composition is not separated from other dosages or servings by packaging. Dosages or servings are delivered from a bulk composition most commonly by a specifically sized measuring apparatus, such as a spoon, cup, or syringe, etc.

As used herein, "PEG" stands for "polyethylene glycol", which is a polymeric ethylene oxide molecule having the general structure $$HO\underset{}{\frown}\left(\underset{}{\frown}O\underset{}{\frown}\right)_n OH,$$

wherein "n" is an integer that is greater than 0. PEG nomenclature can include a number, such as "PEG 3350", wherein the number indicates the average and approximate molecular weight of the polymer.

As used herein, the term "bulk density" refers to the density of a dry composition that has not been disturbed since the composition was introduced into the container from which the density measurement was taken.

As used herein, the term "tapped density" refers to the density of a dry composition that was introduced into the container from which the density measurement would be taken, and the container was tapped to minimize the space between the particles of the composition prior to measuring the density.

As used herein, the term "laxative" refers to a drug or medicine that has the effect of stimulating or facilitating evacuation of the bowels in a subject.

As used herein, the term "supersack" is a large bulk flexible bag container, typically with a liner, net fill weight is approximately 907 kg.

As used herein, when the variation in the amount of sweetener and/or flavoring agent from dose to dose of the bulk composition is "minimized" throughout the dry component laxative composition, the term "minimized" refers to a minimal amount of variation as detected by a spectroscopic method such as HPLC, GC, MS, etc. or a more qualitative method of detection, such as taste.

As used herein the term "about" when preceding a numerical value, indicates that the numerical value can be ±5% of the total value indicated; for example when a measured quantity disclosed herein is "about 100%", the actual quantity could be from 95% to 105%. Unless specified otherwise, when the term "about" precedes a list of more than one numerical value, the term "about" is meant to be applied to all numerical values in the list.

Embodiments of the Invention

In one aspect, the invention includes a dry component bulk laxative composition comprising polyethylene glycol having a molecular weight between 2500 g/mol and 4000 g/mol, a flavoring agent, and optionally a sweetener, wherein the variation in the amount of sweetener and/or flavoring agent from dose to dose of the bulk composition is minimized throughout the dry component laxative composition.

In one embodiment of this aspect, the polyethylene glycol has an average molecular weight of between 3015 g/mol and 3685 g/mol.

In a further embodiment, the polyethylene glycol has an average molecular weight of 3350 g/mol.

In one embodiment, the flavoring agent imparts a flavor selected from but not limited to orange, cherry, grape, strawberry, raspberry, watermelon, blueberry, vanilla, hazelnut, chocolate, coffee, peppermint, caramel, fruit punch, and lemonade to the composition. In a further embodiment, the flavoring agent imparts an orange flavor to the composition.

In still a further embodiment, the flavoring agent is "Trusil Nat & Art Orange Flavor 45467", which is a gum arabic based flavor.

In one embodiment, the composition comprises a sweetener. In a further embodiment, the sweetener is selected from but not limited to glucose, sucrose, maltose, mannose, dextrose, fructose, lactose, trehalose, maltitol, lactitol, xylitol, sorbitol, mannitol, tagatose, glycerin, erythritol, isomalt, maltose, sucralose, aspartame, neotame, alitame, neohesperidin dihydrochalcone, cyclamate, thaumatin, acesulfame potassium, saccharin, saccharin sodium or a combination thereof. In still a further embodiment, the sweetener is sucralose.

In one embodiment, the composition comprises greater than 90 wt % polyethylene glycol. In a further embodiment, the composition comprises greater than 95 wt % polyethylene glycol. In a further embodiment, the composition comprises greater than 98 wt % polyethylene glycol. In still a further embodiment, the composition comprises greater than 99 wt % polyethylene glycol. In still a further embodiment, the composition comprises about 99.33 wt % polyethylene glycol.

In one embodiment, the composition comprises from 0.01 wt % to 10 wt % of a flavoring agent. In a further embodiment, the composition comprises from 0.1 wt % to 2.0 wt % of a flavoring agent. In still a further embodiment, the composition comprises from 0.2 wt % to 1.0 wt % of a flavoring agent. In yet a further embodiment, the composition comprises about 0.58 wt % of a flavoring agent.

In one embodiment, the composition comprises from 0 wt % to 10 wt % of a sweetener. In a further embodiment, the composition comprises from 0.01 wt % to 1.0 wt % of a sweetener. In still a further embodiment, the composition comprises from 0.01 wt % to 0.1 wt % of a sweetener. In yet a further embodiment, the composition comprises about 0.08 wt % of a sweetener.

In one embodiment, the composition has a bulk density of from about 0.5 g/mL to about 1.0 g/mL. In another embodiment, the composition has a bulk density of from about 0.6 g/mL to about 0.8 g/mL. In a further embodiment, the composition has a bulk density of from about 0.62 g/mL to about 0.76 g/mL. In still a further embodiment, the composition has a bulk density of about 0.610 g/mL, about 0.644 g/mL, about 0.670 g/mL, or about 0.672 g/mL.

In one embodiment, the composition has a tapped density of from about 0.5 g/mL to about 1.0 g/mL. In another embodiment, the composition has a tapped density of from about 0.6 g/mL to about 0.9 g/mL. In a further embodiment, wherein the composition has a tapped density of from about 0.68 g/mL to about 0.84 g/mL. In still a further embodiment, the composition has a tapped density of about 0.678 g/mL, about 0.700 g/mL, about 0.744 g/ml, or about 0.764 g/mL.

In one embodiment, the composition comprises PEG powder combined with flavor and, optionally, the sweetener.

In another embodiment, the composition consists essentially of PEG powder having no flavor and no sweetener added, and PEG powder combined with flavor and, optionally, sweetener.

In another aspect, the invention includes a dry component bulk laxative composition comprising:
a. about 99.33 wt % polyethylene glycol having an average molecular weight of about 3350 g/mol;
b. about 0.08 wt % sucralose; and
c. about 0.58 wt % of a flavoring agent;
wherein the composition has a bulk density of about 0.610 g/mL, about 0.644 g/mL, about 0.670 g/mL, or about 0.672 g/mL, and a tapped density of about 0.678 g/mL, about 0.700 g/mL, about 0.744 g/ml, or about 0.764 g/mL;
and wherein the composition consists essentially of PEG powder having no flavor and no sweetener added, and PEG powder combined with flavor and, optionally, sweetener.

In another aspect, the invention includes a process for producing a dry component bulk laxative composition described herein, the process comprising adding the polyethylene glycol, the flavoring agent, and the sweetener, if present, into a blender to form a dry mixture, and blending the dry mixture.

In one embodiment, added to the blender first is a first quantity of polyethylene glycol, second is added the entirety of the sweetener, third is added the entirety of the flavoring agent, and fourth is added a second quantity of polyethylene glycol to form a first mixture, wherein the first quantity and second quantity of polyethylene glycol are approximately the same quantity, the process further comprising blending the first mixture.

In one embodiment, following the first blending period, adding a third and a fourth quantity of polyethylene glycol to the blender, wherein the third and fourth quantity of polyethylene glycol are approximately the same quantity as the first and second quantity of polyethylene glycol to form a second mixture; and blending the second mixture.

In another embodiment, following the second blending period, adding a fifth quantity of polyethylene glycol to the blender, wherein the fifth quantity of polyethylene glycol is approximately the same quantity as the first, second, third, and fourth quantity of polyethylene glycol to form a third mixture; and blending the third mixture.

In one embodiment, the first, second, and third blending periods are performed at a blender speed of 25 revolutions per minute.

In one embodiment, the first, second, and third blending periods are performed at a blender speed of 5.8-25 revolutions per minute.

In another embodiment, the blender speed is about 5.8 revolutions per minute.

In a further embodiment, the invention includes discharging resulting dry component bulk laxative composition into supersacks, then into one or more multiple serving containers and distributing said one or more multiple serving containers to the consumer without further manipulation of the composition.

In another aspect, the invention includes a process for producing a dry component bulk laxative composition as described herein, the process comprising:
a. mixing a first portion of the flavoring agent and a first portion of the sweetener, if present, in a solvent to form a suspension;
b. spraying and depositing the suspension from step a onto a first quantity of polyethylene glycol using a top spray granulation process to form a first mixture;
c. sifting the first mixture from step b to form a second mixture having a consistent particle size of less than 850 microns (passed through a #20 mesh); and
d. optionally, adding to a blender the second mixture from step c, a second quantity of polyethylene glycol, a second portion of the flavoring agent, and a second portion of the sweetener, and blending to produce the dry component bulk laxative composition.

In one embodiment, the solvent in step a is an aqueous solvent.

In one embodiment, the first portion of the flavoring agent in step a is an amount that produces a wt % of 0.29% flavoring in the first mixture.

In one embodiment, the first portion of the sweetener in step a is an amount that produces a wt % of 0.04% in the first mixture.

In another embodiment, the process includes step d.

In one embodiment, the second quantity of polyethylene glycol in step d is eight times the first quantity of polyethylene glycol in step b.

In one embodiment, 25% of the second quantity of polyethylene glycol is first added to the blender; added second to the blender is the first mixture from step c; added third to the blender is a second portion of the sweetener; added fourth to the blender is the second portion of the flavoring agent; and added fifth to the blender is another 25% of the second quantity of polyethylene glycol to make a third mixture.

In a further embodiment, the invention includes blending the third mixture.

In a further embodiment, the invention includes adding the remaining 50% of the second quantity of polyethylene glycol to the third mixture after blending to provide a fourth mixture, and blending the fourth mixture.

In one embodiment, the blending periods are performed at a blender speed of 5.8-25 revolutions per minute.

In another embodiment, the blender speed is about 5.8 revolutions per minute.

In a further embodiment, the invention includes discharging resulting dry component bulk laxative composition into supersacks, then into one or more multiple serving containers and distributing said one or more multiple serving containers to the consumer without further manipulation of the composition.

In another aspect, the invention includes a product made by a process described herein.

In one embodiment, the composition comprises a sweetener, and wherein the concentration of the sweetener in any given local area of the composition remains within 15% of an ideal concentration, wherein the ideal concentration is the predicted concentration of sweetener assuming perfect homogeneity, after the composition is subject to a simulated shipping test, wherein the simulated shipping test comprises the steps of:
a. Placing the composition into a receptacle having a top portion and a bottom portion;
b. Subjecting the receptacle from step a to shaking on a vibration table for a time period of 1 to 10 minutes;
c. Determining the wt % sweetener in a sample of the composition from the top portion of the receptacle;
d. Determining the wt % sweetener in a sample of the composition from the bottom portion of the receptacle; and
e. Comparing the determined wt % values with expected values.

In a further embodiment, the sweetener comprises sucralose.

In another further embodiment, the concentration of the sweetener in any given local area of the composition remains within 10% of the ideal concentration after the composition is subject to the simulated shipping test.

In another further embodiment, the receptacle from step a is subjected to shaking on a vibration table for a time period of 2 minutes or 5 minutes.

In one embodiment, the composition comprises a flavoring agent, and wherein the concentration of the flavoring agent in any given local area of the composition is such that the normalized response calculated from the concentration of flavoring agent in the local area is within 40% of the normalized response after the composition is subject to a simulated shipping test, wherein the simulated shipping test comprises the steps of:
a. Placing the composition into a receptacle having a top portion and a bottom portion;
b. Subjecting the receptacle from step a to shaking on a vibration table for a time period of 1 to 10 minutes;
c. Determining the normalized response for flavoring agent in a sample of the composition from the top portion of the receptacle;
d. Determining the normalized response for flavoring agent in a sample of the composition from the bottom portion of the receptacle; and
e. Comparing the determined normalized response values across sample groupings.

In a further embodiment, the flavoring component comprises limonene.

In another further embodiment, the concentration of the flavoring agent in any given local area of the composition is such that the normalized response calculated from the concentration of flavoring agent in the local area is within 30% of the normalized response across sample groupings.

In another further embodiment, the receptacle from step a is subjected to shaking on a vibration table for a time period of 2 minutes or 5 minutes.

PREPARATIONS AND EXAMPLES

Example 1: Preparation of Direct Blend of PEG 3350, Flavor and Sweetener at Pilot Scale Polyethylene glycol 3350 4.77 kg is added to a 2 cubic foot V-shell blender followed by sucralose 0.02 kg and orange solid flavor 0.14 kg and polyethylene glycol 3350 4.77 kg. The resulting mixture is blended for 5 minutes at 25 rpm. Then polyethylene glycol 3350 9.54 kg is added to the mixture contained in the blender and blended for 5 minutes at 25 rpm. Then polyethylene glycol 3350 4.77 kg is added to the mixture contained in the blender and blended for 20 minutes at 25 rpm. The mixture is then discharged into a drum to be manually packaged in bottles.

Using the general strategy provided in FIG. 1, a batch size of 24.0 kg was made using the following:

| | |
|---|---|
| Equipment | 2 cu. ft. V shell blender |
| Unflavored PEG 3350 | 17000 mg/dose |
| Flavoring agent | Orange solid flavor (100 mg/dose) |
| Sweetener | Sucralose (14 mg/dose) |
| Blending | 20 minute final blending at 25 revolutions per minute |
| Bulk density (starting PEG) | 0.69 g/mL |
| Tapped density (starting PEG) | 0.77 g/mL |
| Bulk density (product composition) | 0.672 g/mL |
| Tapped density (product composition) | 0.764 g/mL |

Figure 3:
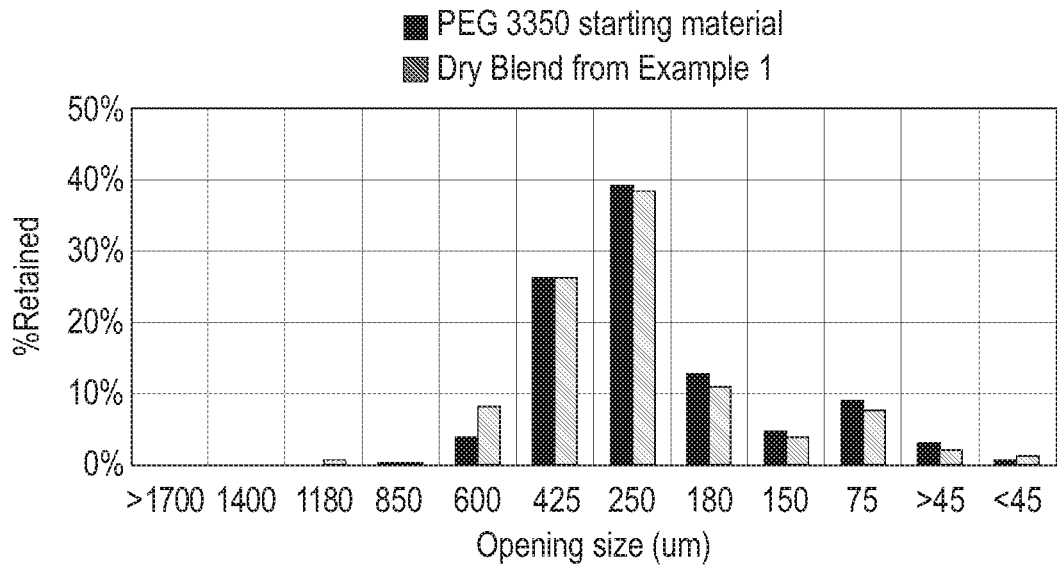
FIG. 3 is a bar graph of particle size distribution, comparing the product of Example 1 to the starting material.

The particle size distribution of this exemplary product in comparison to the unflavored starting PEG is provided in FIG. 3.

Example 2: Preparation of Top Spray Granulation of PEG 3350, Flavor and Sweetener at Lab Scale A suspension of solid orange flavor 86.36 g, sucralose 20.15 g and purified water 319.52 g is prepared by stirring with overhead mixer for approximately 30 minutes. Polyethylene glycol 3350 4893.49 g is added to a Vector FLM X-5 bowl. The PEG 3350 is mixed and preheated to a target product temperature of 42-45° C. with sufficient airflow to achieve proper fluidization. The mixture is then granulated by spraying the suspension at 7 mL/min onto the PEG 3350. The material is discharged from the granulator for further processing.

Figure 2:
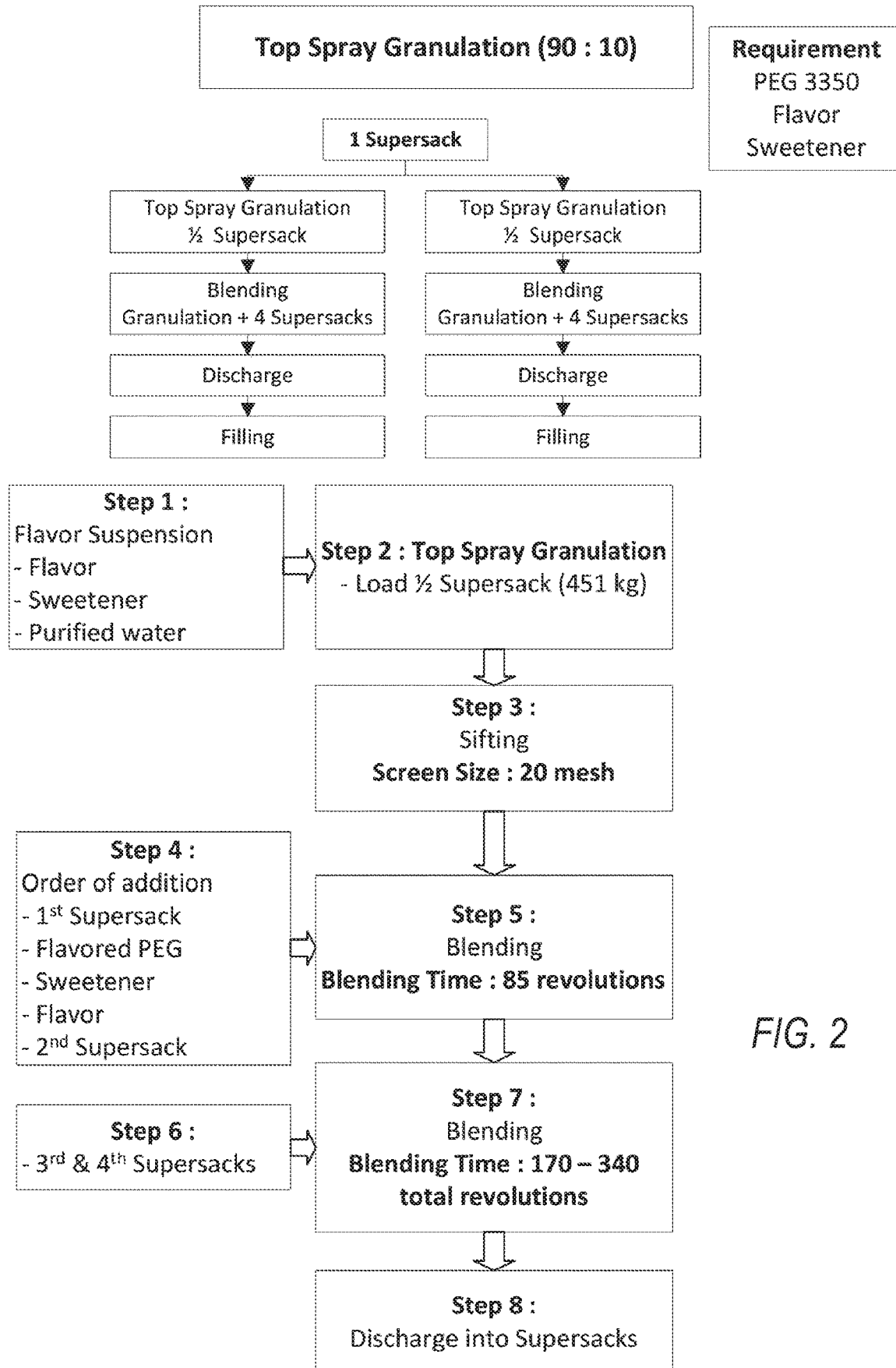
FIG. 2 is a flow chart depicting a top spray granulation and final blend process for producing a single batch of a PEG composition that further comprises a flavoring agent and sweetener.

Using the general strategy provided in FIG. 2, a batch size of 5.0 kg was made using the following:

| | |
|---|---|
| Equipment | Vector FLM X-5 |
| Unflavored PEG 3350 | 1700 mg/dose (Intragranular) |
| Flavoring agent | Orange solid flavor (30 mg/dose) |
| Sweetener | Sucralose (7 mg/dose) |
| Top spray solution | 25% w/w solids (dissolved) in purified water |
| Top spray process air flow | 194 cfm (min)-209 cfm (max) |
| Top spray product temperature | 43° C. (min)-44° C. (max) |
| Bulk density (starting PEG) | 0.669 g/mL |
| Tapped density (starting PEG) | 0.760 g/mL |
| Bulk density (product composition) | 0.644 g/mL |
| Tapped density (product composition) | 0.700 g/mL |

Figure 4:
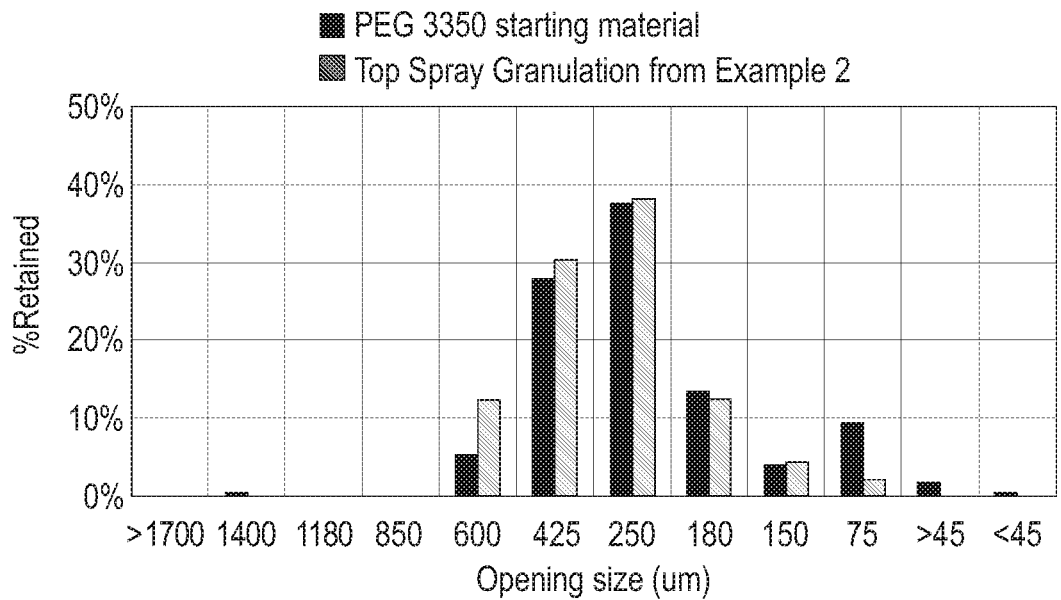
FIG. 4 is a bar graph of particle size distribution, comparing the product of Example 2 to the starting material.

The particle size distribution of this exemplary product in comparison to the unflavored starting PEG is provided in FIG. 4.

Example 3: Preparation of Top Spray Granulation of PEG 3350, Flavor and Sweetener at Pilot Scale Top Spray Granulation:

A suspension of solid orange flavor 1.55 kg, sucralose 0.22 kg and purified water 7.07 kg is prepared by stirring with overhead mixer for approximately 30 minutes. Polyethylene glycol 3350 52.73 kg is added to a Glatt GPCG30 bowl. The PEG 3350 is mixed and preheated to a target product temperature of 41-45° C. with sufficient airflow to achieve proper fluidization. The mixture is then granulated by spraying the suspension at 80-120 g/min onto the PEG 3350. The resulting granulation is dried for 5 minutes then cooled to product temperature of <35° C. in the GPCG30. After discharge, the resulting granulation is passed through a vibratory sieve with #20 mesh (850 micron).

Using the general strategy provided in FIG. 2, a batch size of 54.5 kg was made using the following:

| | |
|---|---|
| Equipment | GPCG30 |
| Unflavored PEG 3350 | 1700 mg/dose (Intragranular) |
| Flavoring agent | Orange solid flavor (50 mg/dose) |
| Sweetener | Sucralose (7 mg/dose) |
| Top spray solution | 20% w/w solids (dissolved) in purified water |
| Top spray process air flow | 494 cfm (min)-581 cfm (max) |
| Top spray product temperature | 36° C. (min)-40 (max) ° C. |
| Vibratory sieve | # 20 mesh (850 micron) |
| Bulk density (starting PEG) | 0.680 g/mL |
| Tapped density (starting PEG) | 0.773 g/mL |
| Bulk density (product composition) | 0.610 g/mL |
| Tapped density (product composition) | 0.678 g/mL |

Figure 5:
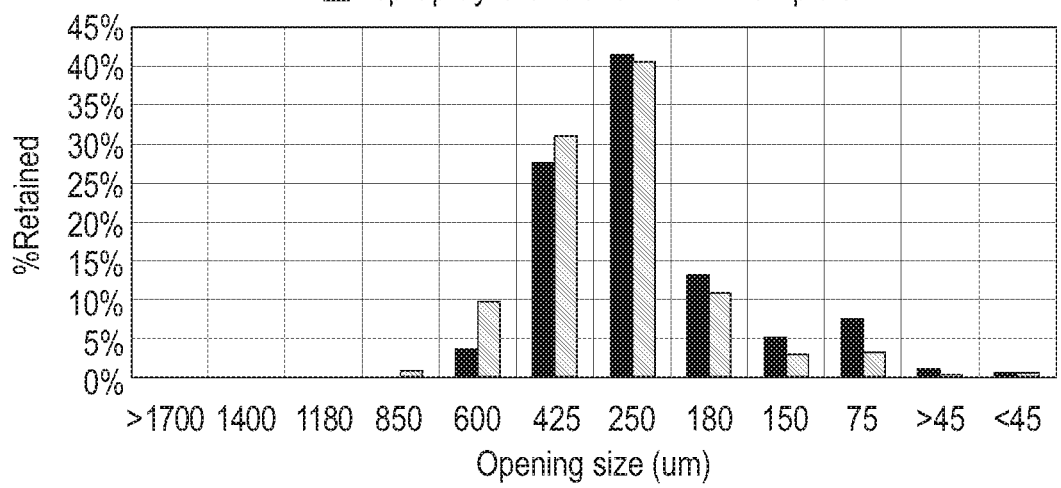
FIG. 5 is a bar graph of particle size distribution, comparing the product of Example 3 to the starting material.

The particle size distribution of this exemplary product in comparison to the unflavored starting PEG is provided in FIG. 5.

Example 4: Preparation of Final Blend of Top Spray Granulation of PEG 3350, Flavor and Sweetener with Extragranular Flavor, Sweetener and PEG 3350 at Pilot Scale Final Blend of Top Spray Granulation Polyethylene glycol 3350 5.37 kg is added to a 2 cubic foot V-shell blender followed by the sifted top spray granulation 2.46 kg, sucralose 0.01 kg, orange solid flavor 0.07 kg and Polyethylene glycol 3350 5.37 kg. The resulting mixture is blended for 5 minutes at 25 rpm. Then Polyethylene glycol 3350 10.73 kg is added to the mixture contained in the blender and blended for 20 minutes at 25 rpm. The mixture is then discharged into a drum to be manually packaged in bottles.

Using the general strategy provided in FIG. 2, a batch size of 24.0 kg was made using the following:

| | |
|---|---|
| Equipment | 2 cu. ft. V-shell blender |
| Composition | 90:10 unflavored PEG:flavored PEG |
| Unflavored PEG 3350 | 1700 mg/dose (Intragranular) + 15300 mg/dose (Extragranular) = 17000 mg/dose total |
| Flavoring agent | Orange solid flavor (100 mg/dose total: 50 mg/dose intragranular, 50 mg/dose extragranular) |
| Sweetener | Sucralose (14 mg/dose total: 7 mg/dose intragranular, 7 mg/dose extragranular) |
| Blending | 20 minute final blending at 25 revolutions per minute |
| Bulk density (unflavored PEG) | 0.69 g/mL |
| Tapped density (unflavored PEG) | 0.77 g/mL |
| Bulk density (product composition) | 0.670 g/mL |
| Tapped density (product composition) | 0.744 g/mL |

Figure 6:
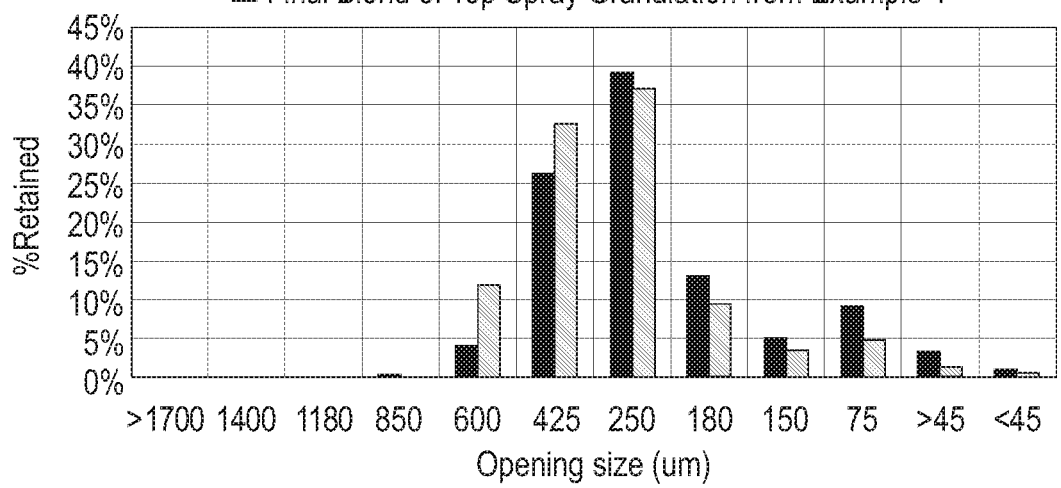
FIG. 6 is a bar graph of particle size distribution, comparing the product of Example 4 to the starting material.

The particle size distribution of this exemplary product in comparison to the unflavored starting PEG is provided in FIG. 6.

Example 5: Simulated Shipping Study Summary

Sample bottle preparation, stressing sample bottles and taking samples for analysis:

To simulate the conditions a bulk flavored powder product may experience during shipping, a simulated shipping study was conducted. Two formulation processes, direct blend vs. final blend of top spray granulation, were evaluated. Flavored powders were manually filled into bottles of 2 sizes (7 doses (4.1 oz) and 30 doses (17.9 oz)) by weight. These bottles were placed into 1 of 2 box sizes, each corresponding to a bottle size (12 bottles per box). The placement of each of the 2 formulation type bottles were randomly assigned to distribute the formulations evenly throughout each box. One box per test/pallet was subjected to shaking on a vibration table for a given period (2 or 5 minutes) at 100% power as a worst-case. Un-stressed sample boxes were also taken to the location of the stress test but not subjected to shaking on the vibration table. The purpose of these samples was to capture any segregation due only to the physical transport of the boxes and bottles to the building/area. Replicate tests were also performed at each condition. The position of direct blend bottles and final blend of top spray granulation bottles in the boxes were swapped for the replicate tests. After completion of the shaking, the boxes were transported back to the lab for sampling. Randomly selected sample bottles were pulled from the same location in each box for sampling and subsequent analysis. Two sets of samples were measured out with the dosing cap and taken from top and bottom of each bottle. One set of samples having sucralose or limonene (component of orange flavor) was for analytical assay to determine the uniformity of sweetener and flavor before and after exposure to the simulated shipping study. The other of samples were for taste perception testing (if needed). The 5 minutes stress samples were tested first as a worst-case scenario. It should be noted that additional control bottles were manually filled to understand variability due to the manual bottle filling process.

Analytical Methods and Results

Sucralose (Sweetener)

Product powder (20 g) was extracted with 25.0 mL of 200 proof ethanol by stirring with a magnetic stir bar. Once extracted completely, samples were centrifuged for 10 minutes at 3000 rpm and diluted 2.0 mL into 20 mL with mobile phase for analysis. High pressure liquid chromatography (HPLC) with refractive index detection was used to compare peak areas against an external standard of sucralose, providing quantitative analysis of sucralose content.

Sucralose (Sweetener) Uniformity Results

Displayed below are attributes and quantitative sucralose results for the simulated shipping study. As the sucralose method was capable of quantitative assessment, the amounts displayed below can be used for quantitative and variability assessment.

TABLE 1

Summary of sucralose concentration results for direct blend samples in 7 dose (4.1 oz) bottles

| Description | Bottle #/Location[1] | Position | % wt/wt | % of Expected[2] in Formula | Sucralose - Average % of Expected[2] | % RSD per sample set |
|---|---|---|---|---|---|---|
| Direct Blend Pre-Stress Bottles | 1 | Top | 0.078% | 94.8% | 107.0% | 27.6% |
| | | Bottom | 0.081% | 98.9% | | |
| | 2 | Top | 0.087% | 105.6% | | |
| | | Bottom | 0.080% | 97.6% | | |
| | 3 | Top | 0.077% | 93.8% | | |
| | | Bottom | 0.085% | 103.1% | | |
| | 4 | Top | 0.069% | 83.8% | | |
| | | Bottom | 0.146% | 178.3% | | |
| Direct Blend Post Stress Bottles (5 min test) | 1 | Top | 0.084% | 102.1% | 99.7% | 12.5% |
| | | Bottom | 0.073% | 89.5% | | |
| | 2 | Top | 0.078% | 95.6% | | |
| | | Bottom | 0.090% | 109.9% | | |
| | 6 | Top | 0.096% | 117.6% | | |
| | | Bottom | 0.072% | 88.0% | | |
| | 8 | Top | 0.069% | 83.7% | | |
| | | Bottom | 0.091% | 111.6% | | |

[1]Location column indicates the section of the test box that the test sample resided (see FIG. 8).
[2]"Expected" refers to the expected signal based on the wt % of sweetener added to the composition, assuming a perfectly homogenous mixture.

TABLE 2

Summary of sucralose concentration results for direct blend samples in 30 dose (17.9 oz) bottles

| Description | Bottle #/Location[1] | Position | % wt/wt | % of Expected[2] in Formula | Sucralose - Average % of Expected[2] | % RSD per sample set |
|---|---|---|---|---|---|---|
| Direct Blend Pre-Stressed Bottles | 1 | Top | 0.073% | 88.6% | 120.8% | 59.4% |
| | | Bottom | 0.070% | 85.7% | | |
| | 2 | Top | 0.081% | 98.2% | | |
| | | Bottom | 0.080% | 97.9% | | |
| | 3 | Top | 0.076% | 92.1% | | |
| | | Bottom | 0.097% | 118.2% | | |
| | 4 | Top | 0.073% | 89.0% | | |
| | | Bottom | 0.243% | 296.8% | | |
| Direct Blend Pre-Stress Bottles | N/A | Top | 0.079% | 96.0% | 91.1% | N/A |
| | | Bottom | 0.071% | 86.3% | | |
| Direct Blend Post-Stress Bottles (5 min test) | 1 | Top | 0.087% | 106.1% | 95.6% | 11.8% |
| | | Bottom | 0.067% | 81.7% | | |
| | 2 | Top | 0.070% | 84.9% | | |
| | | Bottom | 0.073% | 89.3% | | |
| | 3 | Top | 0.072% | 88.0% | | |
| | | Bottom | 0.074% | 90.0% | | |
| | 7 | Top | 0.077% | 93.9% | | |
| | | Bottom | 0.097% | 118.2% | | |

TABLE 2-continued

Summary of sucralose concentration results for direct blend samples in 30 dose (17.9 oz) bottles

| Description | Bottle #/Location[1] | Position | % wt/wt | % of Expected[2] in Formula | Sucralose - Average % of Expected[2] | % RSD per sample set |
|---|---|---|---|---|---|---|
| | 12 | Top | 0.085% | 104.1% | | |
| | | Bottom | 0.081% | 99.4% | | |

[1]Location column indicates the section of the test box that the test sample resided (see FIG. 8).
[2]"Expected" refers to the expected signal based on the wt % of sweetener added to the composition, assuming a perfectly homogenous mixture.

Limonene (Component of Orange Flavor)

Product powder (20 g) was extracted with 25.0 mL of neat DMSO by stirring with a magnetic stir bar. Approximately 10 grams of each sample extract was placed into a 20 mL headspace vial for analysis by headspace gas chromatography with flame ionization detection (HS GC-FID). The peak areas of limonene were normalized and then used for determination of precision for each sample set.

The normalized response (NR) represents a qualitative value for limonene content and was calculated according to Equation 1 below for each sample provided.

$$\text{Normalized Response} = (X \cdot Y)/(W \cdot Z) \quad \text{(Equation 1)}$$

wherein

X=Integrated area of the sample peak in the gas chromatogram;

Y=Weight of the total extraction (additive weight of the sample of dry composition plus extracting solvent, e.g. DMSO);

W=Weight of the sample slurry after transfer to head space (HS) vial; and

Z=Weight of the sample of dry composition prior to extraction.

Displayed below are attributes and normalized responses for the orange flavor shipping study and additional control samples. Table 3 provides the Normalized Response for sample containing limonene.

TABLE 3

Summary of normalized response for limonene content in direct blend samples in 7 dose (4.1 oz) bottles

| Sample Name | Location[1] | Sample Type | Strata | Study | NR |
|---|---|---|---|---|---|
| L4-Top | L4 | Sample | Top | Shipping | 167 |
| L4-Bottom | L4 | Sample | Bottom | Shipping | 207 |
| L5-Top | L5 | Sample | Top | Shipping | 188 |
| L5-Bottom | L5 | Sample | Bottom | Shipping | 255 |
| L9-Top | L9 | Sample | Top | Shipping | 204 |
| L9-Bottom | L9 | Sample | Bottom | Shipping | 309 |
| L10-Top | L10 | Sample | Top | Shipping | 183 |
| L10-Bottom | L10 | Sample | Bottom | Shipping | 232 |
| L12-top | L12 | Sample | Top | Shipping | 150 |
| L12-Bottom | L12 | Sample | Bottom | Shipping | 290 |
| Direct blend-control-Top | Control | Control | Top | Shipping | 247 |
| Direct blend-control-Bottom | Control | Control | Bottom | Shipping | 285 |
| Direct blend-control-Top 1 | Control | Add. Cntrl | Top | Add. Cntrl | 350 |
| Direct blend-control-Top 2 | Control | Add. Cntrl | Top | Add. Cntrl | 340 |
| Direct blend-control-Top 3 | Control | Add. Cntrl | Top | Add. Cntrl | 296 |
| Direct blend-control-Top 4 | Control | Add. Cntrl | Top | Add. Cntrl | 298 |
| Direct blend-control-Top 5 | Control | Add. Cntrl | Top | Add. Cntrl | 247 |
| Direct blend-control-Bottom 1 | Control | Add. Cntrl | Bottom | Add. Cntrl | 294 |
| Direct blend-control-Bottom 2 | Control | Add. Cntrl | Bottom | Add. Cntrl | 358 |
| Direct blend-control-Bottom 3 | Control | Add. Cntrl | Bottom | Add. Cntrl | 337 |
| Direct blend-control-Bottom 4 | Control | Add. Cntrl | Bottom | Add. Cntrl | 268 |
| Direct blend-control-Bottom 5 | Control | Add. Cntrl | Bottom | Add. Cntrl | 362 |
| Precision Sample | N/A | Std | N/A | Shipping | 132 |
| Precision Sample | N/A | Std | N/A | Shipping | 126 |
| Precision Sample | N/A | Std | N/A | Shipping | 146 |
| Precision Sample | N/A | Std | N/A | Shipping | 129 |
| Precision Sample | N/A | Std | N/A | Shipping | 135 |
| Precision Sample | N/A | Std | N/A | Shipping | 139 |
| Precision Sample | N/A | Std | N/A | Add. Cntrl | 245 |
| Precision Sample | N/A | Std | N/A | Add. Cntrl | 248 |
| Precision Sample | N/A | Std | N/A | Add. Cntrl | 276 |
| Precision Sample | N/A | Std | N/A | Add. Cntrl | 249 |
| Precision Sample | N/A | Std | N/A | Add. Cntrl | 256 |
| Precision Sample | N/A | Std | N/A | Add. Cntrl | 249 |

Figure 8:
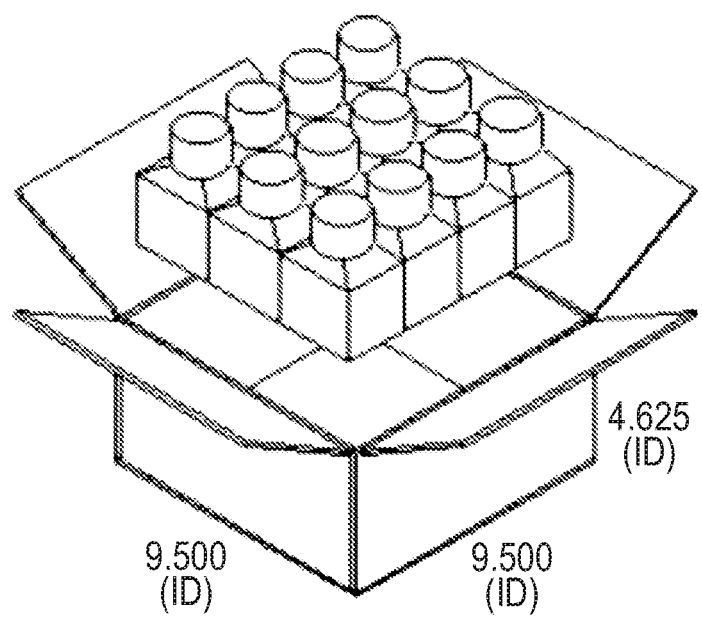
FIG. 8 is a schematic drawing of bottles filled into box for simulated shipping study.

[1]Location column indicates the section of the test box that the test sample resided (see FIG. 8). "Control" in the location column refers to pre-stress samples.

TABLE 4

Summary of normalized response for limonene content in final blend of top spray granulation samples in 7 dose (4.1 oz) bottles

| Sample Name | Location[1] | Sample Type | Strata | Study | NR |
|---|---|---|---|---|---|
| L1-Top | L1 | Sample | Top | Shipping | 245 |
| L1-Bottom | L1 | Sample | Bottom | Shipping | 142 |
| L2-Top-reprep | L2 | Sample | Top | Shipping | 170 |
| L2-Bottom | L2 | Sample | Bottom | Shipping | 192 |
| L6-Top | L6 | Sample | Top | Shipping | 270 |
| L6-Bottom | L6 | Sample | Bottom | Shipping | 136 |
| L8-Top | L8 | Sample | Top | Shipping | 186 |
| L8-Bottom | L8 | Sample | Bottom | Shipping | 160 |
| Top spray-control-Top | Control | Control | Top | Shipping | 193 |
| Top spray-control-Bottom | Control | Control | Bottom | Shipping | 157 |
| Top Spray-control-Top 1 | Control | Add. Cntrl | Top | Add. Cntrl | 290 |
| Top Spray-control-Top 2 | Control | Add. Cntrl | Top | Add. Cntrl | 200 |
| Top Spray-control-Top 3 | Control | Add. Cntrl | Top | Add. Cntrl | 212 |
| Top Spray-control-Top 4 | Control | Add. Cntrl | Top | Add. Cntrl | 200 |
| Top Spray-control-Top 5 | Control | Add. Cntrl | Top | Add. Cntrl | 208 |

TABLE 4-continued

Summary of normalized response for limonene content in final blend of top spray granulation samples in 7 dose (4.1 oz) bottles

| Sample Name | Location[1] | Sample Type | Strata | Study | NR |
|---|---|---|---|---|---|
| Top Spray-control-Bottom 1 | Control | Add. Cntrl | Bottom | Add. Cntrl | 207 |
| Top Spray-control-Bottom 2 | Control | Add. Cntrl | Bottom | Add. Cntrl | 215 |
| Top Spray-control-Bottom 3 | Control | Add. Cntrl | Bottom | Add. Cntrl | 224 |
| Top Spray-control-Bottom 4 | Control | Add. Cntrl | Bottom | Add. Cntrl | 201 |
| Top Spray-control-Bottom 5 | Control | Add. Cntrl | Bottom | Add. Cntrl | 217 |
| Precision Sample | N/A | Std | N/A | Shipping | 132 |
| Precision Sample | N/A | Std | N/A | Shipping | 126 |
| Precision Sample | N/A | Std | N/A | Shipping | 146 |
| Precision Sample | N/A | Std | N/A | Shipping | 129 |
| Precision Sample | N/A | Std | N/A | Shipping | 135 |
| Precision Sample | N/A | Std | N/A | Shipping | 139 |
| Precision Sample | N/A | Std | N/A | Add. Cntrl | 245 |
| Precision Sample | N/A | Std | N/A | Add. Cntrl | 248 |
| Precision Sample | N/A | Std | N/A | Add. Cntrl | 276 |
| Precision Sample | N/A | Std | N/A | Add. Cntrl | 249 |
| Precision Sample | N/A | Std | N/A | Add. Cntrl | 256 |
| Precision Sample | N/A | Std | N/A | Add. Cntrl | 249 |

[1]Location column indicates the section of the test box that the test sample resided (see FIG. 8). "Control" in the location column refers to pre-stress samples.

The particle size distribution of this exemplary product in comparison to the unflavored starting PEG is provided in FIG. 6.

Example 6: Understanding Uniformity and Segregation Potential of Low-Level Flavor and Sweetener within Bulk Drug Product with Differences in Particle Properties Between Active Ingredient and Excipients Purpose Maintaining flavor uniformity throughout use of a bulk powder drug product is important to ensure consistent consumer experience.

Figure 7:
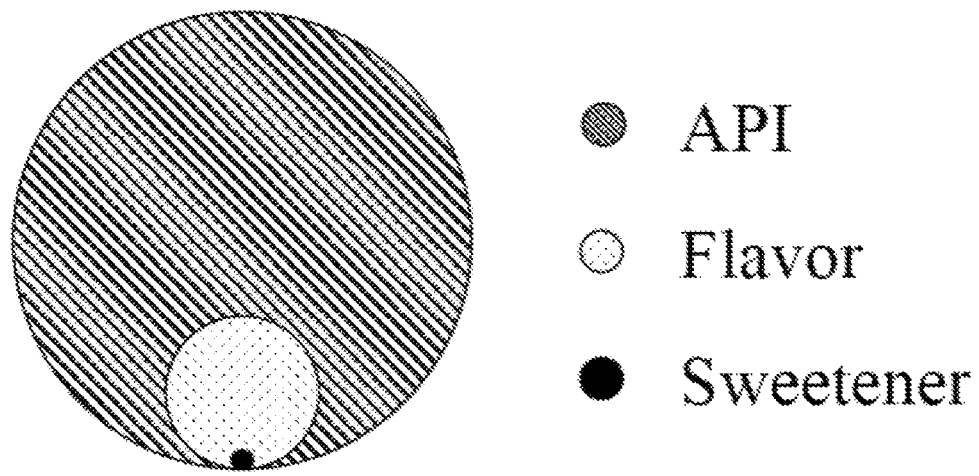
FIG. 7 is a schematic drawing of particle size differences between 3 components (ratios of d90 values represented)

Blend uniformity is typically measured to understand active ingredient uniformity within a drug product, however, this case is unique because here it was important to understand uniformity of "functional" excipients (flavor & sweetener) at very low levels (<1% w/w & <0.1% w/w, respectively) within the drug product 1) initially, and 2) during downstream processing. Especially since particle properties of ingredients used in this drug product are significantly different (FIG. 7), which increases segregation risk.

Bulk density: active ingredient (~0.7 g/mL) and excipients (~0.4 g/mL)

Methods

Drug Product Manufacture

Direct blending process (batch size: 24 kg) was used to distribute flavor & sweetener within the bulk drug product. The blend was manually filled into bottles & packaged into boxes (FIG. 8)

Simulated Shipping Study

Figure 9:
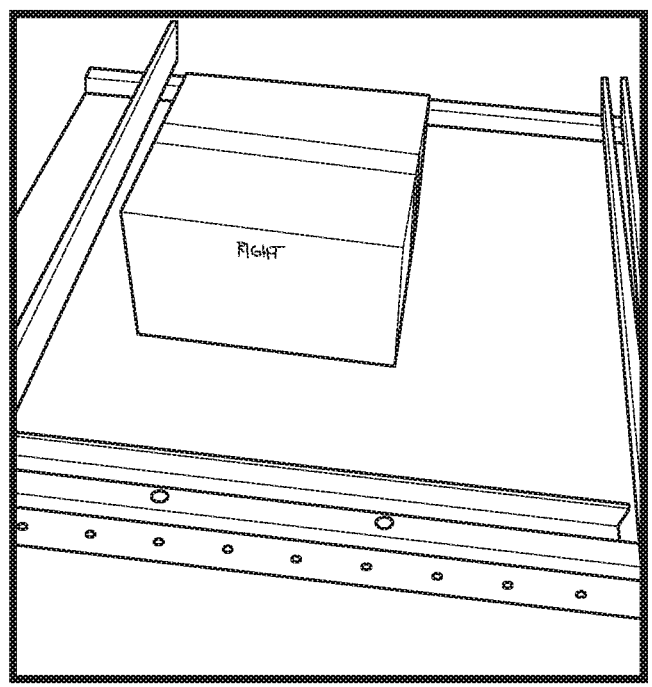
FIG. 9 is an image of box on vibrating table to simulate shipping stress.
Figure 10:
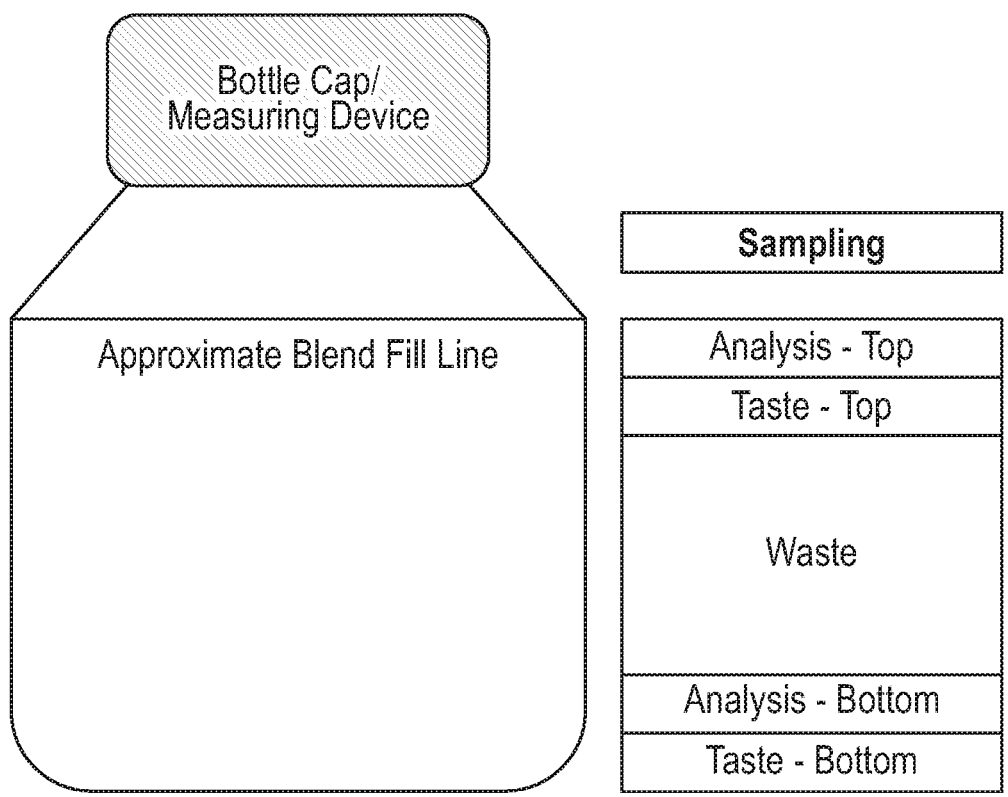
FIG. 10 is a schematic of sampling technique used to simulate end use of product.

Boxes were transported to the testing facility where one box at a time was loaded onto a vibrating table to simulate the stress & shaking conditions of shipment (FIG. 9). The test was run for 5 minutes at 100% speed setting (equivalent to ~1250 miles traveled). The samples were collected volumetrically using the bottle cap as the measuring device to mimic the consumer end-use of the product (FIG. 10). The first ("top") & last ("bottom") doses from each bottle were removed for testing to determine the uniformity of flavor & sweetener in each sample.

Flavor Semi-Quantification

Head Space Gas Chromatography (HS-GC) method with Mass Spectrometer (MS) & Flame Ionization Detector (FID) was used to measure semi-volatile terpene flavor component within final product to semi-quantitatively understand flavor distribution. Due to the complex multicomponent semi-volatile nature of flavors, only relative amount of flavor content was assessed for each sample by utilizing the most abundant component (terpene) as surrogate. Representative sample fractions were prepared in headspace vials using dimethyl sulfoxide as the extraction solvent prior to analysis. Normalized response values were calculated based on peak areas & sample weights.

Sweetener Quantification

High-Performance Liquid Chromatography (HPLC) method with Refractive Index (RI) detection method was used to quantitatively understand sweetener distribution within the representative sample fractions.

Statistical Analysis

Paired student's t-tests were performed to determine statistical significance ($\alpha<0.05$) across sample strata (top vs. bottom). If no difference was found, these sample data were pooled, & an additional paired student's t-test was performed to compare overall pre- & post-stress sample data regardless of strata.

Results

Flavor Semi-Quantitative Analysis

Figure 11A:
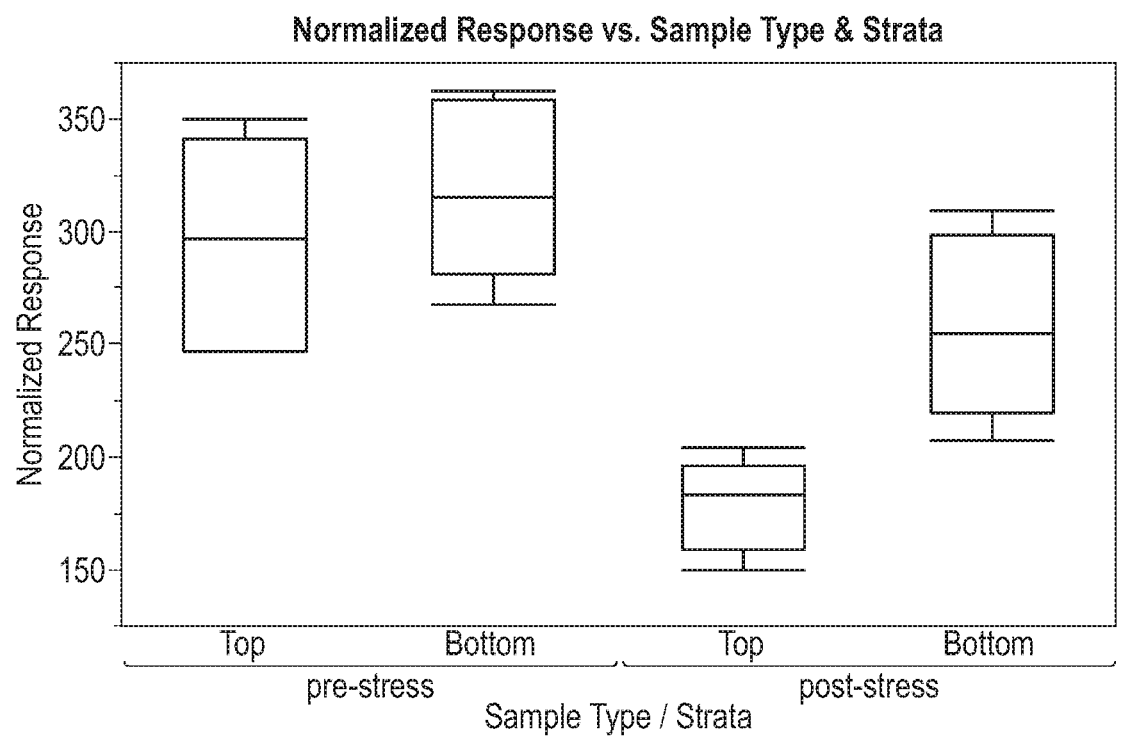
FIG. 11A is a box plot providing the normalized response for flavor component content as a function of sample strata & sample type.
Figure 11B:
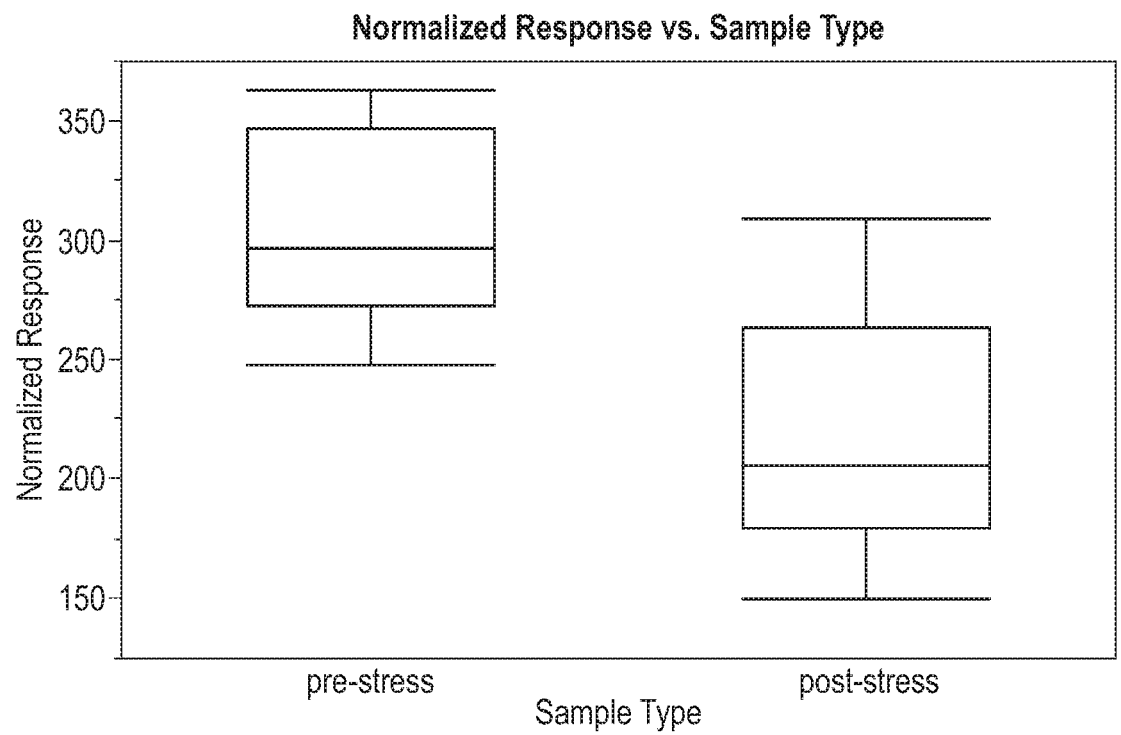
FIG. 11B is a box plot providing the normalized response for flavor component content as a function of sample type.

Normalized response represents a semi-quantitative value for flavor component content and was calculated according to Equation 1. The unit used to express normalized response is not meaningful and should only be used to determine degree of variation between various sample attributes. The flavor component content in pre-stress samples is consistent across sample strata (top vs. bottom) (FIG. 11A). However, a statistically significant difference is observed across strata for the post-stress samples (FIG. 11A & Table 5). The top & bottom sample data were pooled together, and the overall pre- & post-stress sample data were compared, and the difference was also found to be statistically significant (FIG. 11B & Table 5).

Although the differences in flavor content between the top & bottom strata of the post-stress samples and between the pooled pre- & post-stress samples are considered statistically significant, these differences are not functionally or practically significant. This level of change (~30% reduction from target) in flavor content was not perceived by consumers based on taste evaluation.

Sweetener Quantification Analysis

Figure 12A:
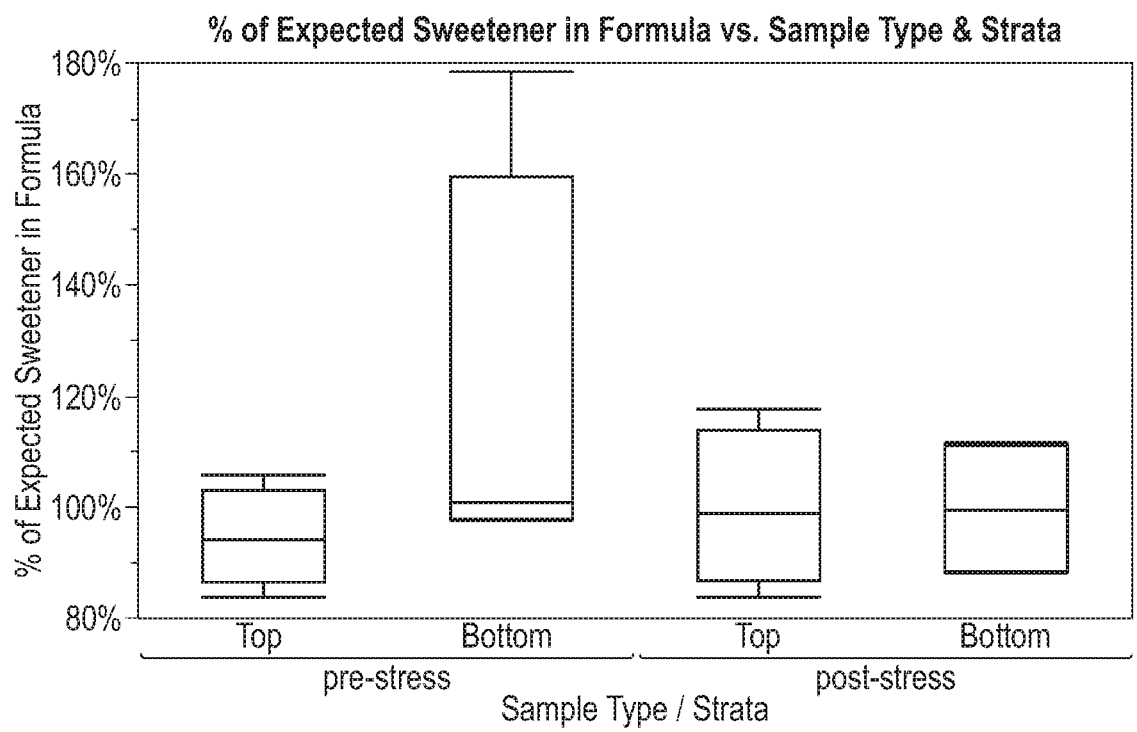
FIG. 12A is a box plot providing sweetener concentration (% of expected level in formula) as a function of sample strata & sample type.
Figure 12B:
FIG. 12B is a box plot providing sweetener concentration (% of expected level in formula) as a function of sample type with outlier run removed from image for better visualization.

The sweetener content (% of expected level in formula) in pre-stress samples as well as post-stress samples is consistent across sample strata (FIG. 12A). Therefore, the top & bottom sample data were pooled together, and the overall pre- & post-stress sample data were compared and are found to be consistent (FIG. 12B & Table 5). These results indicate medium and low risk of segregation of flavor and sweetener, respectively, during downstream processing, and will be further evaluated upon scale up.

TABLE 5

Results of paired student's t-tests

| | Flavor component | | Sweetener | |
|---|---|---|---|---|
| Sample Preparation | t-test p-value | n | t-test p-value | n |
| Pre-stress; top vs. bottom | 0.2005 | 12 | 0.1306 | 8 |
| Post-stress; top vs. bottom | 0.0024* | 10 | 0.5000 | 8 |
| Pre-stress vs. post stress pooled | 0.0001* | 22 | 0.7332 | 16 |

*Statistical significance is shown when p-values are less than α values of 0.05.

Conclusions

Use of a simulated shipping study, HS-GC method for flavor component content & HPLC method for sweetener concentration, determined the uniformity of "functional" excipients at very low levels with different particle properties within the bulk powder drug product. The risk of segregation of these excipients in the bulk drug product initially and during downstream processing (manual bottle filling, simulated shipping & bottle sampling) was established, which guided product development.

OTHER EMBODIMENTS

The foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A dry component bulk laxative composition comprising polyethylene glycol having an average molecular weight of 3350 g/mol, a flavoring agent, and optionally a sweetener, wherein the variation in the amount of flavoring agent and if present, sweetener, from dose to dose of the bulk composition is minimized throughout the dry component laxative composition, such that the concentration of the sweetener, if present, in any given local area of the composition remains within 15% of an ideal concentration, wherein the ideal concentration is the predicted concentration of sweetener assuming perfect homogeneity, after the composition is subject to a simulated shipping test, and the concentration of the flavoring agent in any given local area of the composition is such that the normalized response calculated from the concentration of flavoring agent in the local area is within 40% of the normalized response after the composition is subject to a simulated shipping test, wherein the simulated shipping test comprises the steps of:
  a. Placing the composition into a receptacle having a top portion and a bottom portion;
  b. Subjecting the receptacle from step a to shaking on a vibration table for a time period of 1 to 10 minutes;
  c. Determining the wt ¾ sweetener, or the normalized response for flavoring agent, in a sample of the composition from the top portion of the receptacle;
  d. Determining the wt ¾ sweetener, or the normalized response for flavoring agent, in a sample of the composition from the bottom portion of the receptacle; and
  e. Comparing the determined wt ¾ values with expected values, or comparing the determined normalized response values:

and wherein the dry component bulk laxative composition has a particle size distribution, compared to unflavored starting polyethylene glycol, substantially as shown in FIG. 3, FIG. 4, FIG. 5, or FIG. 6.

2. The composition of claim 1, wherein the flavoring agent imparts a flavor selected from the group consisting of orange, cherry, grape, strawberry, raspberry, watermelon, blueberry, vanilla, hazelnut, chocolate, coffee, peppermint, caramel, fruit punch, and lemonade to the composition.

3. The composition of claim 1, wherein the composition comprises a sweetener.

4. The composition of claim 3, wherein the sweetener is selected from glucose, sucrose, maltose, mannose, dextrose, fructose, lactose, trehalose, maltitol, lactitol, xylitol, sorbitol, mannitol, tagatose, glycerin, erythritol, isomalt, maltose, sucralose, aspartane, neotame, alitame, neohesperidin dihydrochalcone, cyclamate, thaumatin, acesulfame potassium, saccharin, saccharin sodium or a combination thereof.

5. The composition of claim 1, wherein the composition comprises greater than 90 wt % polyethylene glycol.

6. The composition of claim 1, wherein the composition comprises from 0.01 wt % to 10 wt % of a flavoring agent.

7. The composition of claim 1, wherein the composition comprises from 0 wt % to 10 wt % of a sweetener.

8. The composition of claim 1, wherein the composition has a bulk density of from about 0.5 g/mL to about 1.0 g/mL.

9. The composition of claim 1, wherein the composition has a tapped density of from about 0.5 g/mL to about 1.0 g/mL.

10. The composition of claim 1, wherein the composition consists essentially of PEG powder having no flavor and no sweetener added, and PEG powder combined with flavor and, optionally, sweetener.

11. The composition of claim 1, wherein the dry component bulk laxative composition comprises:
  a. about 99.33 wt % polyethylene glycol having an average molecular weight of about 3350 g/mol;
  b. about 0.08 wt % sucralose; and
  c. about 0.58 wt % of a flavoring agent;
  wherein the composition has a bulk density of about 0.610 g/mL, about 0.644 g/mL, about 0.670 g/mL, or about 0.672 g/mL, and a tapped density of about 0.678 g/mL, about 0.700 g/mL, about 0.744 g/ml, or about 0.764 g/mL;
  and wherein the composition consists essentially of PEG powder having no flavor and no sweetener added, and PEG powder combined with flavor and a sweetener.

12. A process for producing a dry component bulk laxative composition according to claim 1, the process comprising adding the polyethylene glycol, the flavoring agent, and the sweetener, if present, into a blender to form a dry mixture, and discharging resulting dry component bulk laxative composition into supersacks, then into one or more multiple serving containers and distributing said one or more multiple serving containers to the consumer without further manipulation of the composition.

13. The process of claim 12, wherein added to the blender first is a first quantity of polyethylene glycol, second is added the entirety of the sweetener, third is added the entirety of the flavoring agent, and fourth is added a second quantity of polyethylene glycol to form a first mixture, wherein the first quantity and second quantity of polyethylene glycol are approximately the same quantity, the process further comprising blending the first mixture at a blender speed of 5.8-25 revolutions per minute for a first blending period.

14. The process of claim 13, further comprising, following the first blending period, adding a third and a fourth quantity of polyethylene glycol to the blender, wherein the third and fourth quantity of polyethylene glycol are approximately the same quantity as the first and second quantity of polyethylene glycol to form a second mixture; and blending the second mixture at a blender speed of 5.8-25 revolutions per minute for a second blending period.

15. The process of claim 14, further comprising, following the second blending period, adding a fifth quantity of polyethylene glycol to the blender, wherein the fifth quantity of polyethylene glycol is approximately the same quantity as the first, second, third, and fourth quantity of polyethylene glycol to form a third mixture; and blending the third mixture at a blender speed of 5.8-25 revolutions per minute for a third blending period.

16. A process for producing a dry component bulk laxative composition according to claim 1, the process comprising:
   a. mixing a first portion of the flavoring agent and a first portion of the sweetener, if present, in a solvent to form a suspension;
   b. spraying and depositing the suspension from step a onto a first quantity of polyethylene glycol using a top spray granulation process to form a first mixture;
   c. sifting the first mixture from step b to form a second mixture having a consistent particle size of less than 850 microns pass after passing through a #20 mesh; and
   d. optionally, adding to a blender the second mixture from step c, a second quantity of polyethylene glycol, a second portion of the flavoring agent, and a second portion of the sweetener, and blending at a blender speed of 5.8-25 revolutions per minute to produce the dry component bulk laxative composition; and discharging resulting dry component bulk laxative composition into supersacks, then into one or more multiple serving containers and distributing said one or more multiple serving containers to the consumer without further manipulation of the composition.

17. The process of claim 16, wherein the solvent in step a is an aqueous solvent.

18. The process of claim 16, wherein the first portion of the flavoring agent in step a is an amount that produces a wt % of 0.29% flavoring in the first mixture.

19. The process of claim 16, wherein the first portion of the sweetener in step a is an amount that produces a wt % of 0.04% in the first mixture.

20. The process of claim 16, wherein the process includes step d.

21. The process of claim 20, wherein the second quantity of polyethylene glycol in step d is eight times the first quantity of polyethylene glycol in step b.

22. The process of claim 21, wherein 25% of the second quantity of polyethylene glycol is first added to the blender; added second to the blender is the first mixture from step c; added third to the blender is a second portion of the sweetener; added fourth to the blender is the second portion of the flavoring agent; and added fifth to the blender is another 25% of the second quantity of polyethylene glycol to make a third mixture.

23. The process of claim 22, further comprising adding the remaining 50% of the second quantity of polyethylene glycol to the third mixture after blending to provide a fourth mixture.

24. The composition according to claim 1, wherein the sweetener comprises sucralose.

25. The composition according to claim 24, wherein the concentration of the sweetener in any given local area of the composition remains within 10% of the ideal concentration after the composition is subject to the simulated shipping test.

26. The composition according to claim 1, wherein the receptacle from step a is subjected to shaking on a vibration table for a time period of 2 minutes or 5 minutes.

27. The composition according to claim 1, wherein the concentration of the flavoring agent in any given local area of the composition is such that the normalized response calculated from the concentration of flavoring agent in the local area is within 30% of the normalized response across sample groupings.

* * * * *